United States Patent [19]

Yang

[11] Patent Number: 5,441,939

[45] Date of Patent: Aug. 15, 1995

[54] 3"-DESMETHOXY DERIVATIVES OF ERYTHROMYCIN AND AZITHROMYCIN

[75] Inventor: Bingwei V. Yang, Waterford, Conn.

[73] Assignee: Pfizer Inc., New York, N.Y.

[21] Appl. No.: 206,551

[22] Filed: Mar. 4, 1994

[51] Int. Cl.$^6$ .................. A61K 31/70; C07H 17/08
[52] U.S. Cl. ...................... 514/29; 536/7.2; 536/7.4
[58] Field of Search ............... 536/7.2, 7.4; 514/29

[56] References Cited

U.S. PATENT DOCUMENTS

| | | | |
|---|---|---|---|
| 4,382,085 | 5/1983 | Sciavolino et al. | 514/29 |
| 4,474,768 | 10/1984 | Bright | 514/29 |
| 4,517,359 | 5/1985 | Kobrehel et al. | 536/7.4 |
| 4,518,590 | 5/1985 | Hauske et al. | 514/29 |
| 4,526,889 | 7/1985 | Bright | 514/29 |
| 4,575,497 | 3/1986 | Omura et al. | 514/30 |
| 4,826,820 | 5/1989 | Brain | 514/29 |

FOREIGN PATENT DOCUMENTS

| | | |
|---|---|---|
| 0137132 | 4/1985 | European Pat. Off. |
| 0503932 | 9/1992 | European Pat. Off. |
| 0503949 | 9/1992 | European Pat. Off. |
| 0508699 | 10/1992 | European Pat. Off. |
| 0508725 | 10/1992 | European Pat. Off. |

OTHER PUBLICATIONS

Molander et al, J. Org. Chem. 1986, 51, 1135–1138.
Bright et al., J. Antibiotics, vol. XLI, No. 8, 1029–1047 (1988).
Gasc. et al., J. Antibiotics, vol. 44, No. 3, 313–330 (1991).
Egan et al., J. Org. Chem., vol. 39, No. 17, 2492–2494 (1974).
Djokic et al., J. Chem. Soc. Pekin Trans. 1, 1881 (1986).

Primary Examiner—Douglas W. Robinson
Assistant Examiner—Elli Peselev
Attorney, Agent, or Firm—Peter C. Richardson; Gregg C. Benson; James T. Jones

[57] ABSTRACT

A compound having the formula

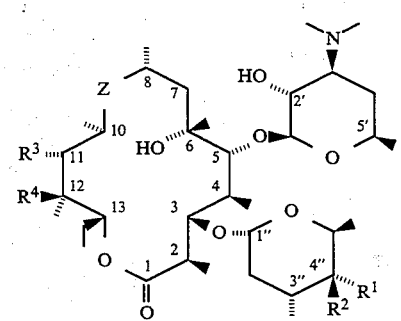

(IV)

wherein
Z is $CH_2-N(CH_3)$, $N(CH_3)-CH_2$, or

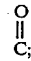

$R^1$ and $R^2$ are selected from
1) one of $R^1$ and $R^2$ is OH and the other of $R^1$ and $R^2$ is $(C_1-C_6)$alkyl, $(C_2-C_6)$alkenyl, or phenyl, with the proviso that Z is not CO;
2) one of $R^1$ and $R^2$ is H and the other of $R^1$ and $R^2$ is $NR^5R^6$ wherein $R^5$ and $R^6$ are independently selected from H and $(C_1-C_6)$alkyl, or is $OR^7$ wherein $R^7$ is H or $(C_1-C_6)$alkyl; and
3) $R^1$ and $R^2$ together form an oxo or oxime group;
$R^3$ and $R^4$ are each hydroxyl or together form a carbonate or thiocarbonate group; and pharmaceutically acceptable salts thereof.

11 Claims, No Drawings

3"-DESMETHOXY DERIVATIVES OF ERYTHROMYCIN AND AZITHROMYCIN

FIELD OF THE INVENTION

This invention relates to antibiotics, and particularly relates to 3"-desmethoxy azithromycin, 3"-desmethoxy erythromycin, and derivatives thereof. These new compounds are useful as antibacterial agents in mammals, including man.

BACKGROUND OF THE INVENTION

Erythromycin is an antibiotic formed during the culturing of a strain of *Streptomyces erythreus* in a suitable medium as taught in U.S. Pat. No. 2,653,899. Erythromycin, which is produced in two forms, A and B, is represented by the following structure (I):

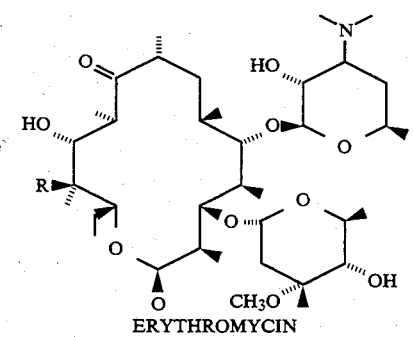

ERYTHROMYCIN

| Erythromycin | R |
|---|---|
| A | —OH |
| B | —H |

The structure reveals that the antibiotic is comprised of three main portions: a sugar fragment known as cladinose, a second sugar moiety containing a basic amino substituent known as desosamine and a fourteen membered lactone ring referred to as erythronolide A or B or as the macrolide ring. Azithromycin is the U.S.A.N. (generic name) for 9a-aza-9a-methyl-9-deoxo-9a-homoerythromycin A, a broad spectrum antibacterial compound derived from erythromycin A. Azithromycin was independently discovered by Bright, U.S. Pat. No. 4,474,768 and Kobrehel et al., U.S. Pat. No. 4,517,359, both of which are herein incorporated by reference, and was named N-methyl-11-aza-10-deoxo-10-dihydro-erythromycin A in these patents. It has the following structure (II) wherein the numbering system conventionally employed is shown:

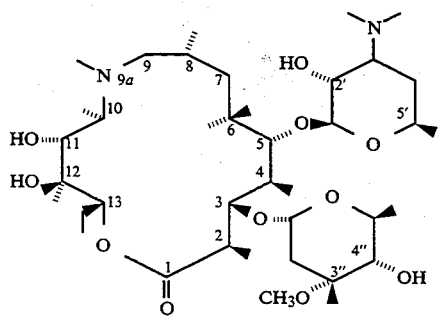

The above patents also disclose that (II) and certain derivatives thereof possess antibacterial properties.

European Patent Applications 0508699A1, 0503932A1, and 0503949A1 (Merck & Co. Inc.) relate to 9-deoxo-8a-aza-8a-homoerythromycin A derivatives, including those having the formula

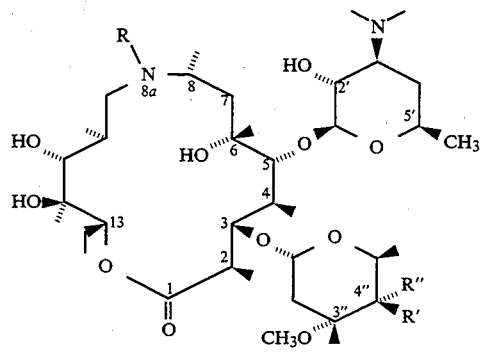

wherein R is hydrogen, substituted or unsubstituted $(C_1-C_{10})$alkyl, $(C_2-C_{10})$alkenyl, or arylsulfonyl, and (among other values) one of R' and R" is hydrogen and the other is selected from hydroxyl, aralkylcarbonyloxy, amino, or amino substituted by any of $(C_1-C_{10})$alkylcarbonyl, arylcarbonyl, aryl$(C_1-C_{10})$alkylcarbonyl, $(C_1-C_{10})$alkoxycarbonyl, aryl$(C_1-C_{10})$alkoxycarbonyl, heteroarylcarbonyl, heteroarylalkylcarbonyl or arylsulfonyl, and the pharmaceutically acceptable salts and esters thereof.

SUMMARY OF THE INVENTION

This invention provides compounds having the formula

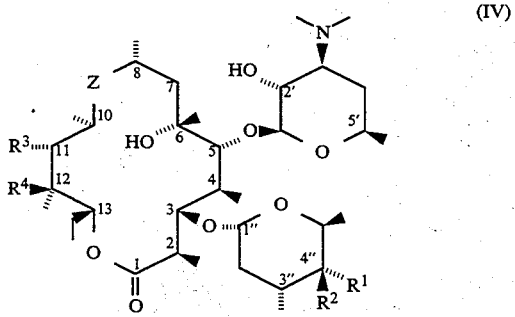

wherein

Z is $CH_2$—$N(CH_3)$, $N(CH_3)$—$CH_2$, or

$R^1$ and $R^2$ are selected from
1) one of $R^1$ and $R^2$ is OH and the other of $R^1$ and $R^2$ is $(C_1-C_6)$alkyl, $(C_2-C_6)$alkenyl, or phenyl, with the proviso that Z is not CO;
2) one of $R^1$ and $R^2$ is H and the other of $R^1$ and $R^2$ is $NR^5R^6$ wherein $R^5$ and $R^6$ are independently selected from H and $(C_1-C_6)$alkyl, or is $OR^7$ wherein $R^7$ is H or $(C_1-C_6)$alkyl; and
3) $R^1$ and $R^2$ together form an oxo or oxime group;

$R^3$ and $R^4$ are each hydroxyl or together form a carbonate or thiocarbonate group;

and pharmaceutically acceptable salts thereof.

The invention further provides pharmaceutical compositions suitable for the treatment of bacterial infections, comprising a compound of formula IV, wherein all variables are as previously defined, or a pharmaceutically acceptable salt thereof, and a pharmaceutically acceptable diluent or carrier.

The invention further provides a method of treating a bacterial infection in a mammalian subject, which comprises administering thereto an antibacterially effective amount of a macrolide antibiotic compound of formula IV or a pharmaceutically acceptable acid addition salt thereof, wherein all variables are as previously defined.

When Z is $CH_2$—$N(CH_3)$, the claimed compounds correspond to 3''-desmethoxy derivatives having a 9-deoxo-8a-aza-8a-homoerythromycin A macrolide ring, i.e., of the type shown as the macrolide ring in formula III above.

When Z is $N(CH_3)$—$CH_2$, the claimed compounds correspond to 3''-desmethoxy derivatives having a 9a-aza-9a-methyl-9-deoxo-9a-homoerythromycin A macrolide ring, i.e, of the type shown as the macrolide ring in formula II above.

When Z is

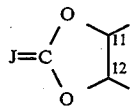

the claimed compounds correspond to 3''-desmethoxy derivatives having an erythromycin macrolide ring, i.e., of the type shown as the macrolide ring in formula I above.

Reference above to $R^3$ and $R^4$ together forming a carbonate or thiocarbonate group refers, in partial structure with appropriate carbons numbered, to the structure

where J is O or S.

The compounds of the invention are useful as broad spectrum antibiotics. They are antibacterial agents which can be used in mammals generally, including man, and are therefore useful in human and veterinary medicine.

DETAILED DESCRIPTION

Compounds of formula IV can be made by processes which include processes known in the chemical arts for the production of structurally analogous compounds. Such processes for the production of a compound of formula IV are provided as further features of the invention and illustrated by the following procedures in which the meanings of generic radicals are as given above unless otherwise qualified. The processes can be effected, generally, for a compound of formula IV, where:

A) $R^1$ and $R^2$ together form an oxo group, by effecting a deoxygenation (i.e., removal of the 3''-methoxy group) of a compound having formula V

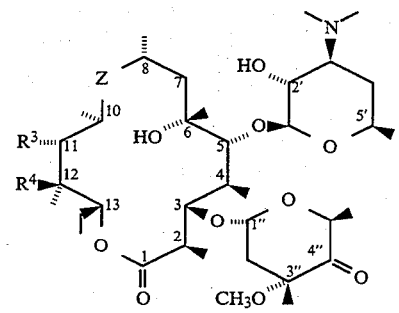

with samarium iodode, $SmI_2$. The reaction can be conducted along the lines presented in J. Org. Chem., 51, 1135–1138, (1986). The reaction can be conducted in a suitable solvent or mixture of solvents, for example tetrahydrofuran (THF) or a mixture of THF and methanol, and at a temperature of −78° C. The product can be isolated by means of conventional organic workup, for example by quenching with aqueous carbonate (e.g., potassium carbonate), evaporating to remove THF, extracting the aqueous phase with ethyl acetate, separating off the ethyl acetate layer, washing the ethyl acetate layer with water, drying with any conventional drying agent such as anhydrous sodium sulfate or magnesium sulfate, and evaporating to yield the product.

B) $R^1$ and $R^2$ together form an oxo group, by converting a compound having the formula

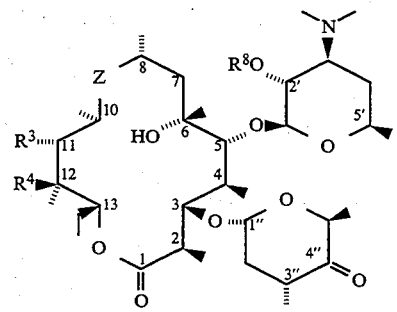

wherein $R^8$ is ($C_2$-$C_4$)alkylcarbonyl, to the corresponding 2'-hydroxy compound. $R^8$ is preferably acetyl. The conversion can be effected as a simple deacylation by solvolysis with a lower alcohol such as methanol or ethanol at room temperature, or higher to increase the rate of reaction. Generally, the conversion can be conducted by simply dissolving a compound of formula VI in alcohol for a time period varying anywhere from a few minutes to several hours. The desired product can be isolated by removal of the solvent, e.g. by evaporation.

C) $R^1$ and $R^2$ together form a 4''-oxime (=N—OH) group, by treating a corresponding 4''-oxo compound with hydroxylamine hydrochloride. The reaction can, for example, be implemented along the lines presented in U.S. Pat. No. 4,512,982 to Hauske, herein incorporated by reference. The reaction can be conducted in a suitable solvent such as a ($C_1$-$C_3$)alcohol, e.g, methanol, at room temperature for several hours. The reaction can optionally be conducted in the presence of a base such as an alkali metal or alkaline earth metal carbonate, with barium carbonate preferred. The hydroxylamine is used in equivalence or, preferably, in excess. Typically, hydroxylamine is used in an amount of 5 equivalents per equivalent of 4″-oxo compound. Workup is conventional and is effected, for example, by removing the alcohol solvent (e.g, by evaporation) in vacuo followed, if desired, by the addition of a mixture of water and ethyl acetate. Product can be isolated by drawing off the ethyl acetate layer and evaporating.

D) one of $R^1$ and $R^2$ is H and the other of $R^1$ and $R^2$ is amino, by reducing the corresponding 4″-oxime with an appropriate reducing agent such as hydrogen over a Raney nickel catalyst. The chemistry is essentially the same as that presented in the '982 Hauske patent mentioned above. The reaction is conducted typically by shaking, at room temperature, the 4″-oxime in a solvent such as a $(C_1-C_3)$alcohol, e.g., ethanol, over Raney Nickel and under a low pressure of hydrogen, typically 50 psi. Workup is conventional and can be effected by filtration to remove the catalyst followed by evaporation of alcohol solvent.

E) one of $R^1$ and $R^2$ is H and the other of $R^1$ and $R^2$ is $NR^5R^6$ wherein $R^5$ and $R^6$ are independently selected from H and $(C_1-C_6)$alkyl, provided that at least one of $R^5$ and $R^6$ is other than H, by conducting, at room temperature, a reductive amination of a corresponding 4″-amino compound with a corresponding $(C_1-C_6)$aldehyde in a suitable solvent such as a chlorinated hydrocarbon (e.g., methylene chloride or dichloroethane), in the presence of a suitable reducing agent such as sodium borohydride, sodium cyanoborohydride, or sodium triacetylborohydride, and in the presence of an organic acid such as acetic or propionic acid. If one of $R^5$ and $R^6$ is H and the other is $(C_1-C_6)$alkyl, then one equivalent of $(C_1-C_6)$aldehyde is employed. If each of $R^5$ and $R^6$ is $(C_1-C_6)$alkyl and both are the same, then two equivalents of $(C_1-C_6)$aldehyde should be employed. If both $R^5$ and $R^6$ are $(C_1-C_6)$alkyl but are different, then two corresponding $(C_1-C_6)$aldehydes, one equivalent each, should be employed sequentially. Workup can be effected by quenching with water, extracting with ethyl acetate, and evaporating solvent.

F) one of $R^1$ and $R^2$ is H and the other of $R^1$ and $R^2$ is $OR^7$ wherein $R^7$ is $(C_1-C_6)$alkyl, by converting a compound of formula VII

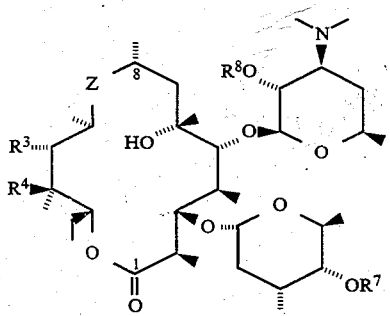

wherein $R^8$ is $(C_2-C_4)$alkylcarbonyl, to the corresponding 2′-hydroxy compound. $R^8$ is preferably acetyl. The conversion can be effected as a simple deacylation with a lower alcohol, as described above for (B); Workup to isolate the product can be affected by solvent evaporation.

G) one of $R^1$ and $R^2$ is H and the other of $R^1$ and $R^2$ is OH, by reducing a corresponding 4″-oxo compound of formula VIII

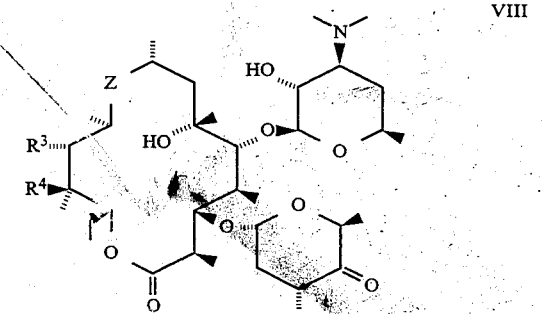

with a suitable reducing agent, for example sodium borohydride or a reducing agent of formula Al-$(OR^9)_3H$ wherein $R^9$ is a $(C_2-C_4)$alkyl group, with lithium aluminum tri-t-butoxy hydride preferred. The reduction can be conducted in a solvent such as THF or diethyl ether, typically from 0° C. to room temperature for a time ranging from minutes to several hours. Reducing agent is present in an equivalents ratio of at least 1:1, and is typically present in excess, say an equivalents ratio of 5:1. A starting material 4″-oxo compound of formula VIII can also be reduced with hydrogen in the presence of Raney Nickel, as described in (D). Workup is conventional and can be conducted using an ethyl acetate/water extraction system preceded by a filtration step if needed to remove catalyst.

H) one of $R^1$ and $R^2$ is OH and the other of $R^1$ and $R^2$ is $R^{10}$ wherein $R^{10}$ is $(C_1-C_6)$alkyl, $(C_1-C_6)$alkenyl, or phenyl, provided that Z is not

by reacting a corresponding compound of formula VIII with a Grignard reagent of formula $R^{10}MgX$ wherein X is a halo group, typically bromo or chloro. The reaction can be conducted in a suitable solvent such as THF or diethyl ether employing an excess of Grignard reagent, typically 5 equivalents of reagent per equivalent of compound VIII. Typically, to the starting material of formula VIII in diethyl ether is added a solution of Grignard reagent and the mixture is stirred at room temperature, typically for about one hour up to several hours, e.g., overnite. A saturated aqueous solution of ammonium chloride can then be added and the aqueous solution extracted with chloroform or ethyl acetate. The organic layer can then be drawn off and evaporated to yield product.

I) $R^3$ and $R^4$ together form a carbonate or thiocarbonate group, by reacting a corresponding compound of formula IV, wherein $R^3$ and $R^4$ are hydroxy, with ethylene carbonate or 1,1-thiocarbonyldiimidazole, respectively, in a suitable solvent such as ethyl acetate, benzene, or a chlorinated lower hydrocarbon. Although the carbonate (or thiocarbonate) is typically formed with a compound of Formula IV, it may also be formed at any intermediate stage, for example using a compound of formulae V, VI, VII, VIII, or IX wherein $R^3$ and $R^4$ are hydroxy. The reaction is typically conducted at reflux temperatures for about 3 to 6 hours. It is preferred that a three to five-fold excess of carbonate or diimidazole to macrolide starting material be employed to ensure substantial completeness of the reaction. The excess can be added at the beginning of the reaction or can be added in divided increments or portions throughout the reaction period. On completion of the period, water is added and the product extracted in the reaction solvent. The solvent is subsequently removed and the residual product purified by conventional means.

The starting materials for use in (A) or (B) above can be made from a corresponding compound of formula IX

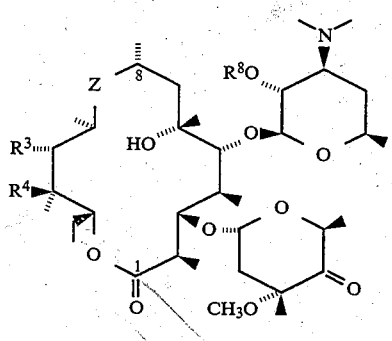

IX by the methodology presented in Bright et al., J. Antibiot., XLI (8), 1029–1047, (1988). To make a compound of formula IX, a corresponding known starting material of formula I, II, or III can be selectively protected by acylation at the 2'-hydroxy group by treating the starting material with an acyl anhydride such as acetic or propionic anhydride in a suitable solvent such as chloroform, at room temperature for several hours, according to standard procedures. The reaction can then be quenched with water, the pH adjusted to 2.5 with 1N HCl, and the organic layer drawn off and discarded. The aqueous pH can then be adjusted to basic (e.g., pH 9.5) with an alkali metal hydroxide and extracted with one or more additional quantities of organic solvent. The organic extraction layer(s) can then be combined and dried (e.g, by filtering through an anhydrous salt such as anhydrous sodium sulfate) and the product isolated by evaporation. The product, now 2'-protected by an acyl group, can then be oxidized under modified Moffat-Pfitzner conditions (DMSO and 1-(3-dimethylaminopropyl)-3-ethylcarbodiimide in the presence of pyridinium trifluoroacetate, along the lines set forth in Bright et al., supra) with stirring, typically for one to several hours to oxidize the 4''-hydroxy group to 4''-oxo. The reaction can be quenched with water and the product (i.e., of formula IX) extracted into ethyl acetate after adjusting the pH of the aqueous reaction medium to basic (ca. 9.5), the solution dried by filtering through an anhydrous salt (e.g., anhydrous magnesium sulfate) and isolated by solvent evaporation.

A compound of formula IX can be deacylated with a lower alcohol, as described in (B), to make a compound of formula V for use as a starting material in (A), supra. Alternatively, the compound of formula IX can first be treated with samarium iodode, as described in (A), to make a compound of formula VI for use as a starting material in (B). The order used for the samarium iodode and deacylation steps is thus not critical.

Once deacylation and samarium iodide reduction have been effected for a compound of formula IX, the product can serve as a starting material for (C), which can in turn serve as a starting material for (D), which can in turn serve as a starting material for (E).

A starting material of formula VIII for use in (G) or (H) can be made by deacylating (i.e., solvolyzing) an appropriate compound of formula VI as described in (B), or deoxygenating an appropriate starting material of formula V as described in (A).

A product made as in (G) can be used to make a corresponding starting material of formula VII for use in (F). The starting material can be made by first selectively acylating the 2'-hydroxy group of a corresponding compound made as described in (G), i.e. wherein one of $R^1$ and $R^2$ is H and the other of $R^1$ and $R^2$ is OH, followed by treating the resulting 2'-acylated compound with a corresponding alkylating agent of formula $R^7X$ where X is a halo group, typically chloro or bromo, and $R^7$ is $(C_1-C_6)$alkyl. The selective acylation can be accomplished as described in Bright et al., J. Antibiot., XLI (8), 1029–1047, (1988) and described above. The alkylation can then be conducted conventionally, in a suitable solvent such as DMSO, a dialkyl ether such as diethyl ether, THF, or a chlorinated hydrocarbon such as methylene chloride, 1,1-dichloroethylene or trichloroethylene. The reaction is conducted in the presence of a base such as an alkali metal or alkaline earth metal carbonate (e.g., sodium carbonate). The reaction is typically conducted for a few minutes to several hours at a temperature from 0° C. to the solvent reflux temperature.

The chemistry useful to make compounds according to the invention can be diagrammed in flow chart form as presented in Scheme I, following, in which conventional symbols have been used, it being noted that a single straight line from a carbon atom indicates a single bond which, stereochemically, can be either up or down.

SCHEME 1

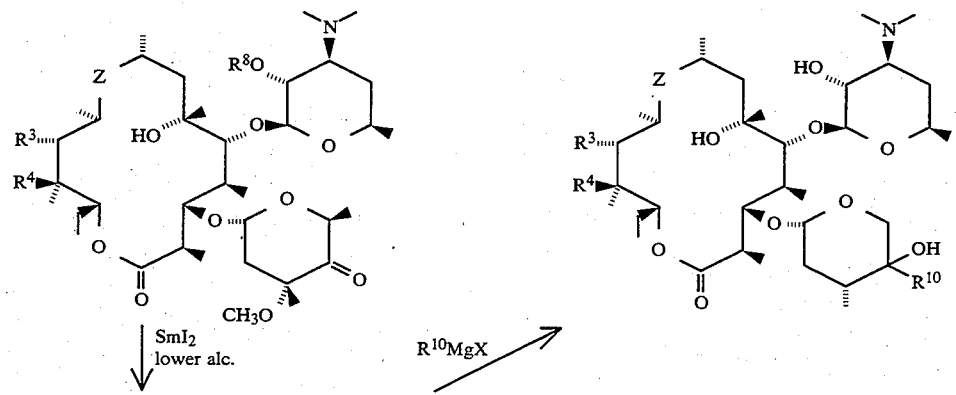

-continued
SCHEME 1

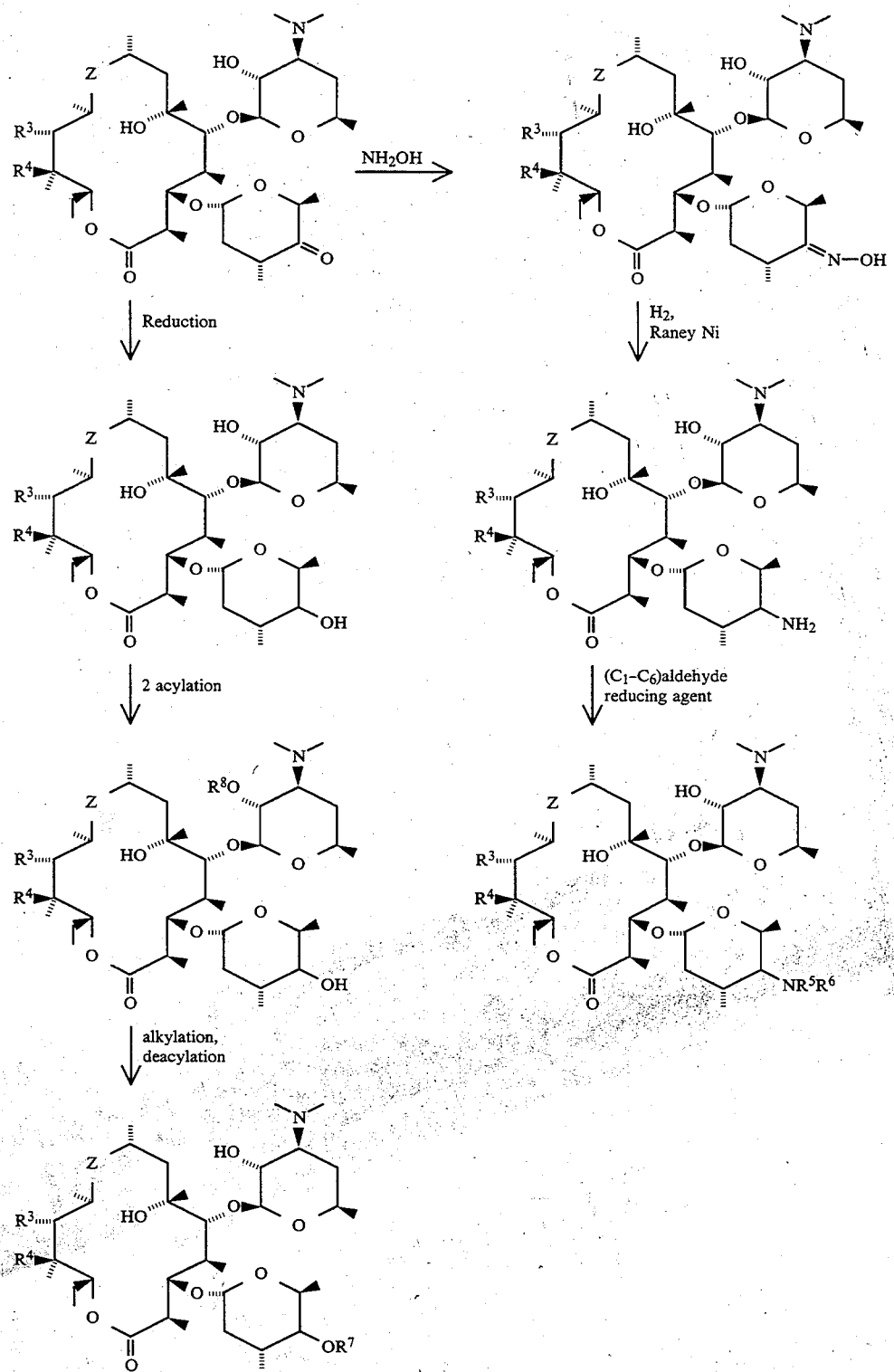

As mentioned previously, the antibacterial agents of this invention and the intermediates used to make them can all be purified or separated from residual materials after preparation, for example if a given preparative reaction is not taken to completion, by standard procedures for macrolide compounds. Such procedures include recrystallization, column chromatography, preparative thin layer chromatography, and counter-current distribution. A preferred mode of purification involves column chromatography using silica gel as the stationary phase and a mixture of chloroform, methanol and 30% aqueous ammonium hydroxide (commercially available, for example, from J. T. Baker) as the eluant. Typically the ammonium hydroxide is present in the eluant in an amount from 0.1–2 volume %, the methanol from 1–10 volume %, with chloroform making up the remainder.

The antibacterial compounds of formula IV are basic and therefore they will form acid addition salts. All such salts are within the scope of this invention, and they can be prepared by standard procedures for macrolide compounds. The compounds contain more than one basic center, and multi-addition acid salts can accordingly be prepared. In general, for preparation of the acid addition salts, a compound of formula IV is combined with a stoichiometric amount of an appropriate acid in an inert solvent, and then the salt is recovered by solvent evaporation, by filtration if the salt precipitates spontaneously, or by precipitation using a non-solvent followed by filtration. Typical salts which can be prepared include sulfate, hydrochloride, hydrobromide, nitrate, phosphate, citrate, tartrate, pamoate, sulfosalicylate, methanesulfonate, benzenesulfonate, and 4-toluenesulfonate salts.

The compounds of formula IV are useful as antibacterial agents both in vitro and in vivo, and their spectrum of activity is similar to that of other known macrolide antibiotics. They can be used in the same manner and for the same purposes as known antibiotics such as erythromycin A and azithromycin.

In general, the compounds of formula IV and salts thereof exhibit in vitro activity against a variety of Gram-positive microorganisms, e.g., *Staphylococcus aureus* and *Streptococcus pyogenes*, and against certain Gram-negative microorganisms such as *E. coli*. Their activity is readily demonstrated by standard in vitro tests against various microorganisms in a brain-heart infusion medium by the usual two-fold serial dilution technique, such as the test described in U.S. Pat. No. 4,526,889 to Bright, the entire text of which is herein incorporated by reference. Their in vitro activity renders them useful for topical application; for sterilization purposes, e.g., sick-room utensils; and as industrial antimicrobials, for example, in water treatment, slime control, and paint and wood preservation. For topical application, it will usually be convenient to prepare pharmaceutical compositions, in which the compound of formula IV is combined with a pharmaceutically-acceptable carrier or diluent, for example in the form of ointments and creams. Appropriate carriers and diluents for these purposes include mineral oils and vegetable oils, and solvents such as water, alcohols, and glycols, and mixtures thereof. Such a pharmaceutical composition will normally contain the pharmaceutically-acceptable carrier and the compound of formula IV in a weight ratio in the range from 4:1 to 1:4.

When used in vivo to treat a bacterial infection in a mammalian subject, especially man, a compound of formula IV, per se or in the form of a pharmaceutically acceptable salt, can be administered alone or in the form of a pharmaceutical composition comprising the compound and a pharmaceutically acceptable diluent or carrier. Such compositions can be administered orally, for example as tablets or capsules, or parenterally, which includes subcutaneous and intramuscular injection. The pharmaceutically acceptable carrier will depend on the intended mode of administration. For example, lactose, sodium citrate, and salts of phosphoric acid, together with disintegrating agents (such as starch) and lubricating agents (such as magnesium stearate, sodium laurel sulfate, and talc) can be used as the pharmaceutically acceptable carrier in tablets. Also, for use in capsules, useful pharmaceutically acceptable carriers are lactose and high molecular weight polyethylene glycols (e.g., having molecular weights from 2,000 to 4,000). For parenteral use, sterile solutions or suspensions can be prepared wherein the pharmaceutically acceptable carrier is aqueous (e.g., water, isotonic saline or isotonic dextrose) or non-aqueous (e.g., fatty oils of vegetable origin such as cottonseed or peanut oil, or polyols such as glycerol or propylene glycol).

For use in vivo of a compound of formula IV, or a salt thereof, a pharmaceutical composition will usually contain the pharmaceutically acceptable carrier and the compound of formula IV or salt thereof in a weight ratio in the range from 4:1 to 1:4.

When used in vivo to treat a bacterial infection in a mammalian subject, either orally or parenterally, the usual daily dosage will be in the range from 5 to 100 mg/kg of body weight, especially 10 to 50 mg/kg of body weight, in single or divided doses.

The following examples and preparations are being provided solely for the purpose of additional illustration. Proton and Carbon-13 nuclear magnetic resonance spectra ($^1$H-NMR, $^{13}$C-NMR spectra) were measured as solutions in deuterated chloroform (CDCl$_3$), and peak positions of diagnostic absorptions are reported in parts per million (ppm). Generally, no internal standard was added. Standard abbreviations have been employed for well known reagents and chemicals: Et$_3$N (triethylamine); MeOH (methanol); EtOH (ethanol); EtOAc (ethyl acetate); and THF (tetrahydrofuran).

EXAMPLE 1

3″R-3″-desmethoxy-4″-deoxy-4″-oxo-9-deoxo-9a-aza-9a-methyl-9a-homoerythromycin A To a solution of SmI$_2$ in THF (0.1M, 170 ml) at −78° C. was added a solution of 2′-acetyl-4″-deoxy-4″-oxo-9-deoxo-9a-aza-9a-methyl-9a-homoerythromycin A (4.55 g, 5.77 mmol) in methanol (15 ml) which was degassed with nitrogen. After 5 min, a saturated aqueous solution of potassium carbonate (10 ml) and water (30 ml) were added and the slurry was gradually warmed up to room temperature. THF was removed in vacuo on a rotary evaporator followed by addition of ethyl acetate (30 ml). The mixture was filtered through celite and the filtrate was separated. The organic layer was washed with brine, dried over magnesium sulfate and concentrated to afford the crude 2′-acetyl-3″-desmethoxy-4″-deoxy-4″-oxo-9-deoxo-9a-aza-9a-methyl-9a-homoerythromycin as a white solid. This solid was dissolved in methanol. The solution was refluxed for 3 hours and allowed to stir at room temperature overnight. The solvent was removed in vacuo, giving the title compounds as a white solid, 4.11 g (5.73 mmol, 99% yield), which contains the 3″R-isomer as the major product.

A pure 3″R sample was obtained after chromatographic purification (silica gel with, in volume %, MeOH/CHCl$_3$/NH$_4$OH:4:95.9:0.1 as eluents), mp 113°–117° C. An X-ray analysis was performed on a single crystal grown from ethyl acetate-hexane.

$^{13}$C NMR (CDCl$_3$) 215.0 (s), 178.3 (s), 103.8 (d), 97.4 (d), 85.2 (d), 79.0 (d), 78.1 (d), 75.6 (d), 74.5 (s), 73.6 (s), 72.0 (d), 71.2 (d), 70.4 (t), 69.4 (d), 65.4 (d), 62.1 (d), 44.6 (d), 42.3 (t), 40.5 (q), 39.4 (d), 37.4 (d), 36.9 (q), 35.3 (t), 29.2 (t), 26.9 (q), 26.7 (d), 21.9 (q), 21.5 (q), 21.1 (t), 16.4 (q), 16.3 (q), 15.8 (q), 13.4 (q), 11.3 (q), 9.5 (q), 7.7 (q). FABHRMS: m/e 717.4920 (M$^+$+H, C$_{37}$H$_{69}$N$_2$O$_{11}$ requires 717.4901).

EXAMPLE 2

3″R,4″R-3″-desmethoxy-9-deoxo-9a-aza-9a-methyl-9a-homoerythromycin A

To a solution of the title compound of example 1 (470 mg, 0.655 mmol) in THF (30 ml) at −78° C. was added a THF solution of lithium tri-tert-butoxy-aluminum hydride (1.0M, 1.0 ml). The reaction mixture was stirred at 0° C. for 3.5 hours then room temperature for 30 min. The reaction was diluted with 30 ml of H$_2$O, and then concentrated in vacuo to remove THF. The resulting basic aqueous solution was extracted with EtOAc (3×30 ml). The combined organic extracts were washed with brine, dried (MgSO$_4$) and concentrated to afford the crude product as a white solid. The crude product was chromatographed on silica gel with MeOH—CHCl$_3$—NH$_4$OH (4:95.9:0.1) as eluents. Three fractions were collected. The fast moving fraction upon evaporation afforded the title compound (4″R-isomer) as a white solid, mp 120°–123° C., 215.5 mg (0.30 mmol, 46 % yield). The slow moving fraction afforded the title compound of example 3 (4S″-isomer), 95 mg (0.132 mmol, 20 % yield). In addition, a mixture of the two isomers were obtained from the middle fraction (132 mg, 0.183 mmol, 28 % yield).

Spectral data of 4″R-isomer: $^{13}$C NMR (CDCl$_3$): 177.3 (s), 105.4 (d), 96.4 (d), 90.2 (d), 84.4 (d), 77.7 (d), 75.4 (d), 75.3 (d), 74.0 (s), 72.9 (s), 71.9 (d), 71.4 (d), 70.8 (t), 68.8 (d), 63.9 (d), 62.2 (d), 44.0 (d), 41.9(t), 40.8 (q), 36.6 (d), 36.5 (q), 32.6 (t), 31.5 (t), 28.1 (d), 26.2 (d), 26.0 (q), 21.3 (q), 20.9 (q), 20.6 (t), 17.3 (q), 15.9 (q), 15.7 (q), 10.8 (q), 9.1 (q), 7.2 (q). HREIMS m/e 718.5049.(M+ for C$_{37}$H$_{70}$N$_2$O$_{11}$ requires 718.4961).

EXAMPLE 3

3″R,4″S-3″-desmethoxy-9-deoxo-9a-aza-9a-methyl-9a-homoerythromycin A

Method A. The title compound was obtained by reduction with lithium tri-tert-butoxy-aluminum hydride followed by chromatography, as described in example 2.

The spectral data: $^{13}$C NMR (CDCl$_3$): 177.7(s), 102.8 (d), 95.9 (d), 85.4 (d), 81.5 (d), 77.6 (d), 75.4 (d), 74.4 (d), 74.2 (s), 73.2 (s), 71.0 (d), 70.6 (t), 70.4 (d), 68.7 (d), 65.9 (d), 62.1 (d), 44.4 (d), 41.9 (t), 40.5(q), 37.9 (d), 36.7 (t), 36.6 (q), 31.3 (d), 29.9 (t), 26.45 (q), 26.4 (q), 21.5 (q), 21.2 (q), 20.8 (t), 18.5 (q), 16.0 (q), 15.9 (q), 13.1 (q), 11.0 (q), 9.1 (q), 7.5 (q). FABHRMS: m/e 719.5055 (M+ +H, C$_{37}$H$_{71}$N$_2$O$_{11}$ requires 719.5039).

Method B To a solution of the title compound of example 1 (52 mg, 0.073 mmol) in methanol (1.5 ml) and ethylene glycol (1 ml) at 0° C. was added sodium borohydride (16 mg, 0.422 mmol). The reaction mixture was stirred at 0° C. for 30 min, then room temperature 30 min. The reaction was diluted with 1 ml H$_2$O and concentrated in vacuo. After addition of H$_2$O-EtOAc and separation, the organic layer was washed with brine, dried (MgSO$_4$) and concentrated in vacuo to afford the title compound as a white solid, 51 mg (0.071 mmol, 97% yield); it was identical with that obtained according to method A.

EXAMPLE 4

3″R-3″-desmethoxy-4″-deoxy-4″-oximino-9-deoxo-9a-aza-9a-methyl-9a-homoerythromycin A A solution of the title compound of example 1 (428 mg, 0.60 mmol) and NH$_2$OH.HCl (208 mg, 3.0 mmol) in methanol (10 ml) was stirred at room temperature for 48 hours. The solvent was removed in vacuo. After addition of 140 ml of EtOAc-H$_2$O (1:1), the pH was adjusted to 9.8 (saturated K$_2$CO$_3$). After separation, the aqueous layer was extracted with ethyl acetate (2×20 ml). The combined organic extracts were washed with brine, dried (MgSO$_4$) and concentrated to afford the title compound as a white solid which contained one of the stereoisomers as the major product, mp 123°–128° C., 412 mg (0.56 mmol, 94% yield).

FABHRMS: m/e 732.4967 (M+ +H, C$_{37}$H$_{70}$N$_3$O$_{11}$ requires 732.4992).

A pure sample of the major isomer (41 mg) was obtained (from the fast moving fraction) after chromatography on silica gel (40% Et$_3$N in toluene).

Spectral data of the major isomer: $^{13}$C NMR (CDCl$_3$): 177.7 (s), 160.0(s), 102.6 (d), 96.0 (d), 85.4 (d), 82.4 (d), 77.8 (d), 75.8 (d), 74.4 (s), 73.4 (s), 71.5 (d), 70.9 (t), 68.8 (d), 65.8 (d), 65.4 (d), 62.3 (d), 44.4 (d), 42.0 (t), 40.7 (q), 40.1 (t), 37.7 (d), 36.9 (q), 30.7 (t), 30.1 (d), 26.5 (d), 21.7 (q), 21.4 (q), 21.0 (t), 16.4 (q), 16.3 (q), 16.2 (q), 11.2 (q), 9.3 (q), 7.8 (q).

EXAMPLE 5

3″R-3″-desmethoxy-4″-deoxy-4″-amino-9-deoxo-9a-aza-9a-methyl-9a-homoerythromycin A A solution of the title compound of example 4 (540 mg, 0.738 mmol) in EtOH (15 ml) was hydrogenated (50 psi pressure, 0.8 g of Raney nickel catalyst) at ambient temperature for 25 hours. Additional 1.15 g of Raney nickel was added and the hydrogenation was continued for another 24 hours. The reaction mixture was filtered through celite and the filtrate was concentrated to afford 344 mg of the crude product. Chromatography on silica gel with CHCl$_3$—MeOH—NH$_4$OH (93.9:6:0.1) as eluents afforded the title compound as a mixture of 4″R and 4″S isomers (about 1:1), mp 133°–137° C., 216 mg (0.301 mmol, 41% yield).

FABHRMS: m/e 717.5117 (M+ +H, C$_{37}$H$_{71}$N$_3$O$_{10}$ requires 717.5121).

EXAMPLE 6

3″R,4″R-3″-desmethoxy-4″-methyl-9-deoxo-9a-aza-9a-methyl-9a-homoerythromycin A

To a solution of the title compound of example 1 (480 mg, 0.669 mmol) in THF (20 ml) was added an ether solution of methylmagnesium bromide (3.0M, 1.5 ml) and the reaction mixture was stirred at room temperature for 1 hour. The reaction was quenched with saturated aqueous NH$_4$Cl and concentrated in vacuo. H$_2$O (20 ml) was added and the pH was adjusted to 9.5 (K$_2$CO$_3$). This was followed by extraction with EtOAc, the combined organic extracts were washed with brine, dried (MgSO$_4$) and concentrated to afford the crude product which was chromatographed on silica gel. A fast moving fraction was collected from silica gel with 2% Et$_3$N in toluene as eluent, which afforded the title compound (4″S-isomer) as a white solid, mp 103°–106° C., 173 mg (0.236 mmol, 35 % yield). A slow moving fraction was also collected with 8% Et$_3$N in toluene as eluent, which afforded 170 mg of the 4″R-isomer, which was further purified by chromatography through silica gel (CHCl$_3$-MeOH—NH$_4$OH: is 95.6/4/0.1) to give a pure sample, mp 110°–115° C., 45 mg (9.2% yield). In addition, a mixture of the 4″R and 4″S isomers, 105 mg (0.143 mmol, 21.4% yield) was obtained from the middle fractions.

Spectral data of 4"R isomer: $^{13}$C NMR (CDCl$_3$): 177.6 (s), 106.1 (d), 96.7 (d), 90.5 (d), 84.9 (d), 80.2 (d), 78.0 (d), 76.2 (d), 74.4 (s), 73.1 (s), 72.4 (d), 71.2 (t), 70.8 (s), 69.1 (d), 64.0 (d), 62.4 (d), 44.2 (d), 42.1 (t), 41.4 (q), 37.0 (q), 36.6 (d), 34.5 (t), 32.8 (t), 32.2 (d), 26.4 (d), 26.0 (q), 21.9 (q), 21.6 (q), 21.2 (q), 20.9 (t), 16.1 (q), 14.74 (q), 14.7 (q), 11.2 (q), 9.5 (q), 7.7 (q). FABHRMS: m/e 733.5207 (M$^+$+H, C$_{38}$H$_{73}$N$_2$O$_{11}$ requires 733.5195).

EXAMPLE 7

3"R,4"S-3"-desmethoxy-4"-methyl-9-deoxo-9a-aza-9a-methyl-9a-homoerythromycin A

The preparation of the title compound is described in example 6.

The spectral data: $^{13}$C NMR (CDCl$_3$): 178.0 (s), 104.2 (d), 97.5 (d), 86.2 (d), 81.4 (d), 77.8 (d), 75.2 (d), 74.4 (s), 73.5 (s), 72.6 (d), 72.1 (s), 71.1 (d), 70.3 (t), 69.0 (d), 65.5 (d), 62.0 (d), 44.7 (d), 42.5 (t), 40.5 (q), 39.3 (d), 36.7 (q), 35.6 (d), 34.5 (t), 29.7 (t), 26.8 (q), 26.6 (d), 21.7 (q), 21.6 (q), 21.3 (q), 21.0 (t), 16.2 (q), 16.0 (q), 15.7 (q), 13.7 (q), 11.1 (q), 9.5 (q), 7.8 (q). FABHRMS: m/e 733.5158 (M$^+$+H, C$_{38}$H$_{73}$N$_2$O$_{11}$ requires 733.5195).

EXAMPLE 8

3"R-3"-desmethoxy-4"-deoxy-4"-oxo-erythromycin A

According to the procedure of example 1, 2'-acetyl-4"-deoxy-4"-oxo-erythromycin A (4.73 g, 6.11 mmol) was treated with SmI$_2$ (0.1M THF solution, 190 ml) in methanol to afford 4.22 g of the crude 2'-acetyl-3"S-3"-desmethoxy-4"-deoxy-4"-oxo-erythromycin A. This was then dissolved in methanol and stirred at room temperature overnight. After removal of methanol, the crude product was chromatographed on silica gel (CHCl$_3$—MeOH—NH$_4$OH:96.9/3/0.1 as eluent) to give the title compound as a white solid, mp 106°–111° C., 2.66 g (3.79 mmol, 62% yield).

$^{13}$C NMR (CDCl$_3$): 222.0 (s), 214.9 (s), 175.5 (s), 104.0 (d), 98.1 (d), 84.1 (d), 79.7 (d), 77.0 (d), 75.0 (s), 74.8 (s), 71.6 (d), 70.9 (d), 69.4 (d), 69.0 (d), 65.3 (d), 45.4 (d), 44.6 (d), 40.3 (q), 38.7 (t), 38.1 (d), 37.3 (d), 37.1 (d), 35.0 (t), 28.6 (t), 26.7 (q), 21.5 (q), 21.2 (t), 18.5 (q), 16.3 (q), 16.0 (q), 15.7 (q), 13.2 (q), 12.1 (q), 10.7 (q), 9.2 (q). FABHRMS: m/e 702.4464 (M$^+$+H, C$_{36}$H$_{64}$NO$_{12}$ requires 702.4411).

EXAMPLE 9

3"R-3"-desmethoxy-erythromycin A

To a solution of the title compound of example 8 (1.6 g, 2.28 mmol) in THF (20 ml) at room temperature was added a THF solution of lithium tri-tert-butoxy-aluminum hydride (1.0M, 3.42 ml). The reaction mixture was stirred at ambient temperature for 30 min. The workup followed the procedure of example 2. The crude product was chromatographed on silica gel with MeOH—CHCl$_3$—NH$_4$OH (3:96.9:0.1) as eluents. The fast moving fraction afforded the title compound as a white solid, mp 116°–119° C., 143 mg (0.203 mmol, 9 % yield).

$^{13}$C NMR (CDCl$_3$): 221.9 (s), 175.2 (s), 105.2 (d), 96.7 (d), 87.4 (d), 83.8 (d), 76.9 (d), 75.2 (d), 74.7(s), 74.6 (s), 71.6 (d), 71.5 (d), 69.3(d), 69.2 (d), 64.5 (d), 45.3(d), 44.2 (d), 40.8 (q), 38.4 (t), 37.9 (d), 37.4 (d), 33.1 (t), 30.7 (t), 28.5 (d), 26.3 (q), 21.23 (q), 21.2 (t), 17.9 (q), 17.2 (q), 16.3 (q), 16.1 (q), 15.3 (q), 12.0 (q), 10.6 (q), 9.2 (q). FABHRMS: m/e 704.4615 (M$^+$+H, C$_{36}$H$_{66}$NO$_{12}$ requires 704.4567).

EXAMPLE 10

3"R-3"-desmethoxy-4"-deoxy-4"-oximino-erythromycin A

A solution of the title compound of example 8 (566 mg, 0.81 mmol), NH$_2$OH.HCl (112 mg, 1.61 mmol) and BaCO$_3$ (637 mg, 3.23 mmol) in methanol (10 ml) was stirred at ambient temperature for 2.5 hours. The workup followed the procedure of example 4. The crude product which contained one of the stereoisomers as the major product was chromatographed on silica gel with MeOH—CHCl$_3$—NH$_4$OH (3:96.9:0.1) as eluents. Two fractions were collected. The slow moving fraction afforded the major isomer of the title compound, mp 148°–151° C., 203 mg (0.283 mmol, 35% yield). The fast moving fraction yielded a mixture of 4"(E) and 4"(Z) isomers, 325 mg (0.45 mmol, 56% yield).

Spectral data of the major isomer: $^{13}$C NMR (CDCl$_3$): 175.3 (s), 161.5 (s), 102.7 (d), 96.8 (d), 83.2 (d), 82.4 (d), 77.3 (d), 76.8 (d), 74.8 (d), 74.7 (s), 70.9 (d), 69.2 (d), 68.9 (d), 65.5 (d), 65.2 (d), 45.4 (d), 44.3 (d), 40.4(q), 39.6 (t), 38.4 (t), 37.7 (d), 30.0 (d), 29.4 (t), 26.8 (q), 21.5 (q), 21.1 (t), 18.2 (q), 16.6 (q), 16.3 (q), 15.8 (q), 15.6 (q), 12.1 (q), 10.6 (q), 9.1(q). FABHRMS: m/e 717.4489 (M$^+$+H, C$_{36}$H$_{65}$N$_2$O$_{12}$ requires 717.4520).

EXAMPLE 11

3"R-3"-desmethoxy-4"-deoxy-4"-amino-erythromycin A

According to the procedure of example 5, the title compound of example 10 (1.00 g, 1.39 mmol) in EtOH (25 ml) was hydrogenated (50 psi pressure, 1.0 g of Raney nickel catalyst) at ambient temperature for 12 hours to afford the title compound as a mixture of 4"R and 4"S-isomers (about 1:1), mp 108°–113° C., 729 mg (1.037 mmol, 74.6% yield).

EI-HRMS: m/e 703.4709 (M$^+$, C$_{36}$H$_{67}$N$_2$O$_{11}$ requires 703.4727).

EXAMPLE 12

3"R-3"-desmethoxy-4"-deoxy-4"-oxo-(11-O, 12-O-oxomethylene)erythromycin A

A solution of the title compound of example 8 (203 mg, 0.283 mmol), ethylene carbonate (249 mg, 1.42 mmol) and K$_2$CO$_3$ (196 mg, 1.42 mmol) in benzene was refluxed overnight. After removal of benzene, the product mixture was dissolved in CHCl$_3$ and washed with 10% aqueous K$_2$CO$_3$, water and brine, dried (MgSO$_4$) and concentrated to afford the title compound as a mixture of 3"R and 3"S-isomers (78:22), mp 99°–104° C, 198 mg (0.266 mmol, 94%

Spectral data of 3"R-isomer: $^{13}$C NMR (CDCl$_3$): 215.5 (s), 177.1 (s), 153.2 (s), 103.7 (d), 95.7 (d), 85.0 (d), 84.9 (d), 77.3 (d), 76.5 (s), 75.9 (d), 73.2 (s), 71.2 (d), 70.3 (d), 69.2 (d), 67.2 (d), 65.1 (d), 60.9 (d), 44.7 (d), 41.0 (d), 40.2 (q), 37.1 (d), 34.9 (t), 34.1 (q), 29.5 (t), 28.5 (t), 26.3 (q), 26.1 (d), 21.1 (q), 15.7 (q), 14.4 (q), 14.0 (q), 12.9 (q), 11.7 (q), 10.2 (q), 5.4 (q). FABHRMS: m/e 743.4703 (M$^+$+H, C$_{38}$H$_{67}$N$_2$O$_{12}$ requires 743.4676).

EXAMPLE 13

3"R-3"-desmethoxy-(11-O, 12-O-oxomethylene)erythromycin A

According to the procedure of example 12, the title compound of example 9 (1.13 g, 1.57 mmol) was reacted with ethylene carbonate (1.33 g, 18.1 mmol) in reflux benzene to afford the title compound as a white solid, top, 96°-99° C., 1.06 g (1.42 mmol, 91% yield).

$^{13}$C NMR (CDCl$_3$): 175.5, 153.4, 105.6, 96.7, 90.1, 86.2, 84.9, 84.0, 77.2, 75.8, 75.5, 72.9, 72.0, 71.6, 69.1, 67.9, 64.2, 61.7, 44.1, 42.1, 41.1, 37.1, 34.8, 32.8, 31.6, 28.3, 26.0, 25.7, 21.7, 21.4, 21.1, 17.4, 15.9, 13.5, 10.5, 9.5. FABHRMS: m/e 745.4910 (M$^+$+H, C$_{38}$H$_{69}$N$_2$O$_{12}$ requires 745.4832).

EXAMPLE 14

3″R ,4″R-3″-desmethoxy-4″-phenyl-9-deoxo-9a-aza-9a-methyl-9a-homoerythromycin A To a solution of the title compound of example 1 (205 mg, 0.286 mmol) in THF (10 ml) was added a THF solution of phenylmagnesium bromide (3.0M, 0.62 ml). The reaction mixture was stirred at room temperature for 20 hours. The workup followed the procedure of example 6. The crude product was chromatographed on silica gel (CHCl$_3$—MeOH—NH$_4$OH:95.9/4/0.1) to afford the title compound as a mixture of 4″S and 4″R-isomers (about 1:1), 40 mg (0.05 mmol, 18% yield.)

FABHRMS: m/e 795.5360 (M$^+$+H, C$_{43}$H$_{75}$N$_2$O$_{11}$ requires 795.5351).

What is claimed is:

1. A compound having the formula

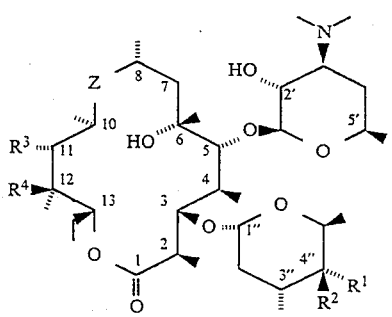

(IV)

wherein
Z is CH$_2$—N(CH$_3$), N(CH$_3$)—CH$_2$, or $$\overset{O}{\underset{}{\overset{\|}{C}}};$$

R$^1$ and R$^2$ are selected from the group consisting of:
1) one of R$^1$ and R$^2$ is OH and the other of R$^1$ and R$^2$ is (C$_1$-C$_6$)alkyl, (C$_2$-C$_6$)alkenyl, or phenyl, with the proviso that Z is not CO;
2) one of R$^1$ and R$^2$ is H and the other of R$^1$ and R$^2$ is NR$^5$R$^6$ wherein R$^5$ and R$^6$ are independently selected from the group consisting of H and (C$_1$-C$_6$)alkyl, or is OR$^7$ wherein R$^7$ is H or (C$_1$-C$_6$)alkyl; and
3) R$^1$ and R$^2$ together form an oxo or oxime group;
R$^3$ and R$^4$ are each hydroxyl or together form a carbonate or thiocarbonate group;
or a pharmaceutically acceptable salt thereof.

2. A compound as defined in claim 1, wherein Z is N(CH$_3$)—CH$_2$.

3. A compound as defined in claim 1, wherein Z is $$\overset{O}{\underset{}{\overset{\|}{C}}}.$$

4. A pharmaceutical composition suitable for the treatment of bacterial infections, comprising an effective amount of a compound as defined in claim 1, or a pharmaceutically acceptable salt thereof, and a pharmaceutically acceptable diluent or carrier.

5. A composition as defined in claim 4, wherein Z is N(CH$_3$)—CH$_2$.

6. A composition as defined in claim 4, wherein Z is $$\overset{O}{\underset{}{\overset{\|}{C}}}$$

7. A method of treating a bacterial infection in a mammalian subject, which comprises administering thereto an antibacterially effective amount of a compound as defined in claim 1, or a pharmaceutically acceptable acid addition salt thereof.

8. A method as defined in claim 7, wherein Z is N(CH$_3$)CH$_2$.

9. A method as defined in claim 7, wherein Z is $$\overset{O}{\underset{}{\overset{\|}{C}}}.$$

10. A compound having the formula

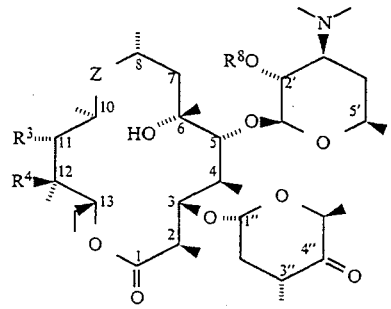

VI wherein R$^8$ is (C$_2$-C$_4$)alkylcarbonyl and R$^3$, R$^4$ and Z are as defined in claim 1.

11. A compound having the formula

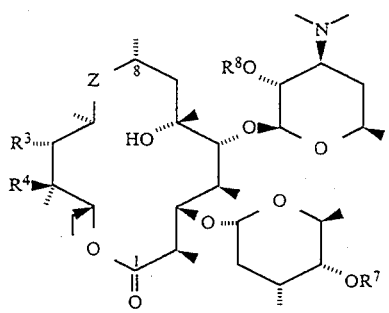

VII wherein R$^8$ is (C$_2$-C$_4$)alkylcarbonyl, R$^7$ is (C$_1$-C$_6$)alkyl, and R$^3$, R$^4$ and Z are as defined in claim 1.

* * * * *